US008273684B2

(12) United States Patent
Tang et al.

(10) Patent No.: US 8,273,684 B2
(45) Date of Patent: Sep. 25, 2012

(54) SEED COATING COMPOSITION

(75) Inventors: Chaucer C. Tang, Kennett Square, PA (US); Donald W. Ward, Fort Madison, IA (US); George R. Wheeler, Fort Madison, IA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/161,671

(22) Filed: Jun. 16, 2011

(65) Prior Publication Data

US 2011/0245078 A1    Oct. 6, 2011

Related U.S. Application Data

(62) Division of application No. 11/586,999, filed on Oct. 26, 2006, now Pat. No. 7,989,391.

(51) Int. Cl.
*A01N 25/26* (2006.01)
(52) U.S. Cl. ........................................ 504/100
(58) Field of Classification Search ............... None
See application file for complete search history.

(56) References Cited

U.S. PATENT DOCUMENTS

| 3,707,807 | A |   | 1/1973  | Graves            |         |
|-----------|---|---|---------|-------------------|---------|
| 4,249,343 | A |   | 2/1981  | Dannelly          |         |
| 4,272,417 | A |   | 6/1981  | Barke et al.      |         |
| 5,219,916 | A | * | 6/1993  | Den Hartog et al. | 524/515 |
| 5,231,131 | A | * | 7/1993  | Chu et al.        | 524/504 |
| 5,849,320 | A |   | 12/1998 | Turnblad et al.   |         |
| 2003/0221365 | A1 |  | 12/2003 | Babler et al.    |         |

OTHER PUBLICATIONS

Product Brochure, Atlox™ SemKote, Uniqema, Inc., pp. 1-5, 2004.
Product Brochure, Celvol® Seed Coating, Celanese Corporation, pp. 1-2, Jun. 2006.

* cited by examiner

*Primary Examiner* — Alton Pryor
(74) *Attorney, Agent, or Firm* — Simon L. Xu

(57) ABSTRACT

The invention pertains to a seed coating composition comprising a certain latex binder and/or graft polymer dispersant. The seed coating composition imparts good color to treated seeds, has excellent durability, and is non-sticky after application to allow for smooth flow of coated seed in planting equipment.

4 Claims, No Drawings

SEED COATING COMPOSITION

BACKGROUND OF THE INVENTION

The invention pertains to a seed coating compositions and more particularly to a seed coating composition comprising a certain latex binder and/or certain graft polymer dispersant.

Seeds are often treated to reduce yield losses during cultivation and for enhancing the agronomic and nutritional value of the produce. Such treating agents are for example fungicides, insecticides, rodenticides, nematocides, miticides or bird repellents. Furthermore, many varieties of genetically altered crops are coming to the market. Treated and/or genetically modified seeds must be marked in order to distinguish them from the untreated and unmodified seeds. The marking of seeds is particularly beneficial for farmers who then can easily distinguish the chemically treated and modified seeds for plantings from e.g. cereal grains for consumption.

Various seed coating ingredients therefore, have been disclosed. For example, U.S. Pat. No. 4,272,417 discloses a seed coating composition comprising a binding agent selected from the class of vinyl acrylic emulsions, partially hydrolyzed copolymers of vinyl chloride and vinyl acetate, polyvinyl alcohols, polyvinyl acetates, drying oil modified polyurethanes, vinyl toluene copolymer modified drying oils, 23 percent penta soya oil alkyd, pinene polymer hydrocarbon resins, chain stopped alkyds, chlorinated rubber, epoxy esters, acrylics, modified polyacrylamides, self-curing carboxylated styrene butadiene latex, polyvinyl pyrrolidone, poly (methyl vinyl ether/maleic anhydride), vinyl pyrrolidone/dimethylamino ethylmethacrylate copolymer, and vinyl pyrrolidone/vinyl acetate copolymer.

U.S. Pat. No. 5,849,320 discloses an insecticidal coating for a seed comprising one or more binders selected from the group consisting of polymers and copolymers of polyvinyl acetate, methyl cellulose, polyvinyl alcohol, vinylidene chloride, acrylic, cellulose, polyvinylpyrrolidone and polysaccharide and an insecticidally effective amount of an insecticide, wherein the binder forms a matrix for the insecticide.

U.S. Pat. No. 4,249,343 discloses compositions for coating plant seeds comprising a water insoluble polymeric microgel that provides protection for the seeds from mechanical and environmental damages and that may be used as a carrier for materials such as fertilizers, herbicide, pesticides and so forth. Useful monomers for the production of microgels by addition polymerization include acrylic acid; methacrylic acid; hydroxy esters, amino substituted esters and amides of acrylic acid, methacrylic acid and maleic acid; vinylpyridine and derivatives of vinyl pyridine such as 2-methyl-5-vinylpyridine.

U.S. Pat. No. 3,707,807 discloses a composition for treating seeds comprising an aqueous emulsion of a substantially water-soluble neutralized copolymer of an α,β-unsaturated monocarboxylic acid and a lower alkyl acrylate and a crosslinked copolymer of vinyl acetate and a lower alkyl acrylate.

U.S. Patent Publication 2003/0221365 discloses pigment forms and pigment concentrates which can be effectively used for seed coloring.

Seed coating compositions and ingredients are also available commercially from, for example, Becker Underwood (Ames, Iowa) under the SEEDKARE® tradename, Uniqema (New Castle, Del.) under the Atlox™ Semkote tradename, International Specialty Products (Wayne N.J.) under the Agrimer® tradename and Celanese Corp. (Dallas Tex.) under the Celvol® tradename.

There is still a need for, and it is an objective of this invention to provide, seed coating compositions that impart good color to treated seeds, that resist attrition and dust formation on handling and that are non-sticky and allow smooth flow of coated seed in planting equipment.

SUMMARY OF THE INVENTION

In accord with an objective of this invention, there is provided a seed coating composition comprising an aqueous carrier, a pigment colorant, and either one or both of (a) an acrylic latex binder and/or (b) a graft copolymer dispersant.

The acrylic latex binder is an acrylic polymer dispersion containing about 30-40% by weight methyl methacrylate, 10-20% by weight styrene, 35-45% by weight 2-ethylhexyl acrylate, 1-6% by weight methylol methacrylamide, 1-5% by weight hydroxyethyl acrylate and 1-5% by weight methacrylic acid; and, wherein the acid groups of the graft copolymer are neutralized with an inorganic base or an amine.

The dispersant is a graft copolymer having a weight average molecular weight of about 5,000-100,000 and comprising a polymeric backbone and macromonomer side chains attached to the backbone wherein: (1) the polymeric backbone is hydrophobic in comparison to the side chains and contains polymerized ethylenically unsaturated hydrophobic monomers and up to 20% by weight, based on the weight of the graft copolymer, of polymerized ethylenically unsaturated acid containing monomers; and (2) the sidechains are hydrophilic macromonomers that are attached to the backbone at a single terminal point and contain polymerized ethylenically unsaturated monomers and 2-100% by weight, based on the weight of the macromonomer, of polymerized ethylenically unsaturated acid containing monomers and have a weight average molecular weight of about 1,000-30,000; and, wherein the acid groups of the graft copolymer are neutralized with an inorganic base or an amine.

The prescribed acrylic latex binder is particularly advantageous for providing a durable, non-sticky coating that effectively binds colorants and other ingredients to treated seeds.

The prescribed graft copolymer dispersant is particularly effective at stably dispersing a range of pigment colorants in an aqueous seed coating carrier comprising binder. Because of the advantageous dispersion properties of the prescribed graft copolymer dispersant, a given color strength can be achieved with less pigment.

DETAILED DESCRIPTION OF THE PREFERRED EMBODIMENTS

Seed Coating Composition

Seed coating compositions comprise an aqueous carrier which can be simply water, or combination of water and other solvent(s), and colorant dispersed or dissolved in the carrier. The composition will typically comprise binder, such as a polymer or resin, dispersed or dissolved in the carrier. The will also typically comprise colorant, especially pigment colorant, and also may comprise a dispersant, such as a polymer or resin dispersant, to stabilize the dispersion of a pigment colorant. Other ingredients known in the art may also be present in the composition including, for example, surfactants, biocides, fungicides, insecticides, fillers and the like.

The seed coating composition according to the present invention will comprise one or both of a prescribed latex binder and/or a prescribed graft copolymer dispersant which species are herein after described. Although not limited to any particular amounts, seed coating compositions will generally contains 0.01 to 10 wt % pigment, and 40 to 98 wt % aqueous carrier. When the prescribed dispersant is present, the pigment to dispersant weight ratio will generally be in the range of about 0.1/100 to 1500/100. When the prescribed acrylic latex binder is present, it will generally be present in an amount of between about 0.5 and 40 wt % (polymer solids basis). All percentages are weight percent (wt %) of the ingredient relative to the final weight of seed coating composition.

Colorant

Seed coatings typically comprise colorant so as to be visually distinguishable. Suitable colorants include charcoal, graphite, iron oxide, tartrazine, titanium dioxide, zinc oxide and organic pigments with C.I. designation Pigment Blue 15, Pigment Green, Pigment Violet 23 and Pigment Red 48. Suitable colorants can also include dyes such as those with C.I. designation Food Red 17, Food Blue 2, Solvent Green, Solvent Red 23, Acid Red 33, Solvent Violet 13, and Basic Blue 9. The "C.I." designation refers to the nomenclature established by Society Dyers and Colourists, Bradford, Yorkshire, UK and published in The Color Index, Fourth Edition, 2002.

Binder

A binder can be any suitable binder approved for agricultural use, One such list of suitable binders can be found in the U.S. Code of Federal Regulations Title 40, Part 180.960 (referred to hereafter as 40CFR 180.960).

Included in this list approved binders are acrylic polymers composed of one or more of the following monomers: acrylic acid, methyl acrylate, ethyl acrylate, butyl acrylate, hydroxyethyl acrylate hydroxybutyl acrylate, carboxyethyl acrylate, methacrylic acid, methyl methacrylate, hydroxy butyl methacrylate, lauryl methacrylate, and stearyl methacrylate; with none and/or one or more of the following monomers: acrylamide, N-methyl acrylamide, N,N-dimethyl acrylamide, N-octyl acrylamide, maleic anhydride, maleic acid, monoethyl maleate, diethyl maleate, monooctyl maleate, dioctyl maleate; and their corresponding sodium, potassium, ammonium, isopropylamine, triethylamine, monoethanolamine, and/or triethanolamine salts. Other suitable binders from this list include: copolymers of methyl vinyl ether with maleic anhydride or monoalkyl esters of maleic anhydride (e.g. Agrimer® VEMA line of products from ISP); polyvinylpyrrolidone; copolymers of vinyl pyrrolidone with vinyl acetate (e.g., Agrimer VA line of products from ISP); copolymers of vinyl pyrrolidone with vinyl alkyls (e.g. Agrimer® AL line of products from ISP); polyvinyl acetate; ethylene/vinyl acetate copolymers (e.g. Atlox® SemKote E product line from Uniqema); vinyl acetate acrylic copolymers (e.g., Atlox® Semkote V product line from Uniqema); A-B block copolymers of ethylene oxide and propylene oxide; A-B-A triblock copolymers of EO-PO-EO (e.g. Pluronics® line from BASF); and polyvinyl alcohol.

A preferred binder is an acrylic latex polymer comprising N-methylol (meth)acrylamide monomer. The term "latex" as used herein means a dispersion in an aqueous carrier of polymer particles having a particle size of about 0.06-0.20 microns and a weight average molecular weight of greater than 500,000. (typically 500,000 to about 3,000,000)

A particularly preferred acrylic latex binder polymer comprises: an acrylic polymer containing about 30-40% by weight methyl methacrylate, 10-20% by weight styrene, 35-45% by weight 2-ethylhexyl acrylate, 1-6% by weight methylol methacrylamide, 1-5% by weight hydroxyethyl acrylate and 1-5% by weight methacrylic acid which binder is described in U.S. Pat. No. 5,219,916, which disclosure is incorporated by reference herein for all purposes as if fully set forth.

The acrylic latex polymer is formed by conventional emulsion polymerization by emulsifying a mixture of monomers, water, surfactant and polymerization catalyst and charging the resulting emulsion into a conventional polymerization reactor and heating the constituents in the reactor to about 60-95° C. for about 15 minutes to 8 hours and then the resulting polymer is neutralized with ammonia or an amine. The size of the polymeric particles of the latex is about 0.06-0.20 microns. The resulting polymer has a hydroxyl no. of 2-100, a glass transition temperature of −40 to +40° C. and a weight average molecular weight of about 500,000-3,000,000.

All molecular weights herein are measured by gel permeation chromatography using polystyrene as the standard.

Typically useful catalysts are ammonium persulfate, hydrogen peroxide, sodium meta bisulfite, hydrogen peroxide, sodium sulfoxylate and the like.

Typically useful surfactants are nonylphenoxypolyethyleneoxy ethanol sulfate, allyl dodecyl sulfosuccinate, alkyl phenoxy polyethylene oxyethanol, sodium lauryl sulfate and mixtures thereof. One preferred surfactant is a mixture of nonylphenoxy polyethyleneoxy ethanol sulfate and allyl dodecyl sulfosuccinate.

The acrylic latex polymer contains about 1-15% by weight of polymerized methylol methacrylamide, methylol acrylamide or any mixtures thereof.

Dispersant

Pigment dispersion stability in aqueous carrier can be increased by the presence of a polymer dispersant or surfactant. Suitable dispersants and surfactants include those commonly used in agricultural and crop protection applications such as those listed in the Code of Federal Regulations Title 40 Parts 180.900, 180.910, and 180.920 (to be referred to hereafter as 40CFR 180.900; 40CFR 180.910; and 40 CFR 180.920, respectively.) That list includes, for example, A-B block copolymers of ethylene oxide and propylene oxide; A-B-A triblock copolymers of EO-PO-EO (e.g. Pluronics® line from BASF); naphthalenesulfonic acid-formaldehyde condensates, ammonium and sodium salts; styrene-maleic anyhydride copolymers; monobutyl/ethyl Ester of poly(methyl vinyl ether/maleic acid), partial sodium salt (e.g. EasySperse Dispersant available from ISP); methyl methacrylate/polyethylene glycol graft copolymer (e.g. Atlox 4913 from Uniqema); random, water-soluble acrylic copolymers (e.g. Metasperse 100L and Atlox® 4914 from Uniqema); nonyl phenol ethoxylates (e.g. Tergitol nonionic surfactants from Dow Chemical); octyl phenol ethoxylates (e.g. Triton nonionic surfactants from Dow Chemical and Igepal product line from Stepan Chemical).

A preferred dispersant is a graft copolymer having a weight average molecular weight of about 5,000-100,000 and comprising a polymeric backbone and macromonomer side chains attached to the backbone and more specifically a graft copolymer dispersant wherein:

(1) the polymeric backbone is hydrophobic in comparison to the side chains and contains polymerized ethylenically unsaturated hydrophobic monomers and up to 20% by weight, based on the weight of the graft copolymer, of polymerized ethylenically unsaturated acid containing monomers; and (2) the sidechains are hydrophilic macromonomers that are attached to the backbone at a single terminal point and contain polymerized ethylenically unsaturated monomers and 2-100% by weight, based on the weight of the macromonomer, of polymerized ethylenically unsaturated acid containing monomers and have a weight average molecular weight of about 1,000-30,000 and wherein the acid groups of the graft copolymer are neutralized with an inorganic base or an amine.

The graft copolymer contains about 50-90% by weight of polymeric backbone and correspondingly about 10-50% by weight of sidechains. The graft copolymer has a weight average molecular weight of about 5,000-100,000 and preferably about 10,000-40,000. The side chains of the graft copolymer are formed from hydrophilic macromonomers that have a weight average molecular weight of about 1,000-30,000 and preferably 2,000-5,000 and contain about 2-100% by weight and preferably 20-50% by weight, based on the weight of the macromonomer, of polymerized ethylenically unsaturated acid monomers. These sidechains are hydrophilic and keep the dispersant and pigments uniformly dispersed in the pigment dispersion and in the resulting coating composition.

The backbone of the graft copolymer is hydrophobic relative to the sidechains and may contain up to 20% by weight, preferably 1-10% by weight, based on the weight of the graft copolymer, of polymerized ethylenically unsaturated acid monomers which are listed hereinafter. The backbone contains polymerized hydrophobic monomers such as alkyl methacrylates and acrylates, cycloaliphatic methacrylates and acrylates and aryl methacrylates and acrylates as are listed hereinafter and also may contain up to 30% by weight, based on the weight of the graft copolymer, of polymerized ethylenically unsaturated non-hydrophobic monomers which may contain functional groups. Examples of such monomers are hydroxy ethyl acrylate, hydroxy ethyl methacrylate, t-butylamino ethyl methacrylate, diethyl amino ethyl acrylate, diethyl amino ethyl methacrylate, acrylamide, nitro phenol acrylate, nitro phenol methacrylate, phthalimido methyl acrylate, phthalimido methacrylate, acrylic acid, acryloamido propane sulfonic acid.

The backbone of the graft copolymer has an affinity for the surface of the pigment used in the dispersion and anchors the copolymer to the pigment and keeps the pigment dispersed and prevents the graft copolymer from returning to the aqueous phase. Reactive groups on the backbone can react with the pigment and form a bond with the pigment.

Molecular weights are determined by Gel Permeation Chromatography using polystyrene as a standard.

The macromonomer contains a single terminal ethylenically unsaturated group which is polymerized into the backbone of the graft copolymer and primarily contains polymerized monomers of methacrylic acid, its esters, nitriles, amides or mixtures of these monomers.

Typical alkyl methacrylates that can be used have 1-8 carbon atoms in the alkyl group and are for example methyl methacrylate, ethyl methacrylate, propyl methacrylate, isopropyl methacrylate, butyl methacrylate, pentyl methacrylate, hexyl methacrylate, 2-ethyl hexyl methacrylate and the like. Cycloaliphatic methacrylates also can be used such as trimethylcyclohexyl methacrylate, isobutylcyclohexyl methacrylate, and the like. Aryl methacrylates also can be used such as benzyl methacrylate. Other polymerizable monomers that can be used are styrene, alpha methyl styrene, methacrylamide and methacrylonitrile. The above monomers can also be used in the backbone of the graft copolymer.

The macromonomer can contain 2-100% by weight, preferably about 20-50% by weight, based on the weight of the macromonomer, of polymerized ethylenically unsaturated acid. Methacrylic acid is preferred particularly if it is the sole constituent. Other acids that can be used are ethylenically unsaturated carboxylic acids such as acrylic acid, itaconic acid, maleic acid and the like. Ethylenically unsaturated sulfonic, sulfinic, phosphoric or phosphonic acid and esters thereof also can be used such as styrene sulfonic acid, acrylamido methyl propane sulfonic acid, vinyl phosphonic acid and its esters and the like. The above acids also can be used in the backbone of the graft copolymer.

Up to 40% by weight, based on the weight of the macromonomer, of other polymerized ethylenically unsaturated monomers can be present in the macromonomer. Primarily alkyl acrylates having 1-12 carbons in the alkyl group can be used such as methyl acrylate, ethyl acrylate, propyl acrylate, isopropyl acrylate, butyl acrylate, pentyl acrylate, hexyl acrylate, 2-ethyl acrylate, nonyl acrylate, lauryl acrylate and the like can be used. Cycloaliphatic acrylates can be used such as trimethylcyclohexyl acrylate, t-butyl cyclohexyl acrylate and the like. Aryl acrylates such as benzyl acrylate also can be used. The above monomers also can be used in the backbone of the graft copolymer.

One preferred macromonomer contains about 50-80% by weight of polymerized methyl methacrylate and 20-50% by weight of polymerized methacrylic acid and has a weight average molecular weight of about 2,000-5,000. To ensure the macromonomer only has one terminal ethylenically unsaturated group which will polymerize with the backbone monomers to form the graft copolymer, the macromonomer is preferably polymerized using cobalt chain transfer agents.

Methods of making graft copolymer dispersant are known and described, for example, in U.S. Pat. No. 5,231,131 which disclosure is incorporated by reference herein for all purposes as if fully set forth.

To form a pigment dispersion or a mill base, pigments are added to the aqueous graft copolymer dispersion and then the pigments are dispersed using conventional techniques such as high speed mixing, ball milling, sand grinding, attritor grinding or two or three roll milling. The resulting pigment dispersion has a pigment to dispersant binder weight ratio of about 0.1/100 to 1500/100.

The preferred graft copolymer dispersant is advantageous in seed coatings with pigment colorant because it provides good color strength on the coated seed, therefore less pigment is needed to achieving a given level of coloration. It also has the advantage of being able to disperse a wide range of pigments both organic and inorganic.

Coated Seeds

The seeds prescribed herein are used to grow plants, fruits, or vegetables. The particular type of seed is not critical. The coating composition is applied to the exterior surface of the seeds and the water and other volatile components are allowed to vaporize leaving the non-volatile components bound to the seed by the binder.

Various techniques and equipment known in the seed coating art may be used for applying the coating composition to the seed. The process may be continuous or batch and typically involves tumbling the seed in the presence of the coating composition. Some drying of the coated seed may be required.

It may be advantageous to "overcoat" the coated seeds with additional binder to encase the seed treating agents and further protect them from attrition during handling.

The following examples illustrate the invention without, however, being limited thereto.

EXAMPLES

Preparation of Graft Copolymer Dispersant

Using the methods described in U.S. Pat. No. 5,231,131 a macromonomer was prepared with contained 28.75% methacrylic acid and 71.25% methyl methacrylate and having a weight average molecular weight of about 4000 and a number average molecular weight of about 2000.

Graft Copolymer 1 was prepared by polymerizing the macromonomer above with butyl acrylate, methyl acrylate and acrylic acid, again following the methods described in U.S. Pat. No. 5,231,131 and having the overall approximate composition: 31.8% butyl acrylate, 31.8% methyl acrylate, 6.4% acrylic acid, 21.4% methyl methacrylate, and 8.6% methacrylic acid and had a weight-average molecular weight of about 24000 and a number-average molecular weight of about 9500. Graft copolymer 1 was neutralized with 2-amino-2-methyl-1-propanol and recovered as a 30 wt % solution in water for subsequent use as a dispersant.

Preparation of Latex Binder

Latex Binder 1 was prepared according to methods described in U.S. Pat. No. 5,219,916 having the following monomer composition: MMA/S/2-EHA/MOLMAM/HEA/MAA in a weight ratio of 26.5/15/50/2.5/3/3. It was neutralized with ammonia to form the ammonium salt and had a weight average molecular weight of about 500,000-1,250,000. Latex 1 had a average particle size was 0.095 microns and was recovered as an aqueous slurry with 35.7 wt % polymer solids. The following abbreviations are used for the monomers: MMA is methyl methacrylate; S is styrene; 2-EHA is 2-ethylhexyl acrylate; MOLMAM is N-methylol methacrylamide; HEA is hydroxyethyl acrylate; and MAA is methacrylic acid.

Example 1

Dispersion 1 was prepared from 100 parts of Latex Binder 1 described above, 3 parts of talc and 0.5 parts of Pigment Red 48:2. Ingredients were mixed and milled in a sand mill with 0.8-1.0 mm zirconia media. The milled dispersion had a Brookfield viscosity (Brookfield viscometer, #3 spindle, 100 rpm, 25° C.) of 197 cps and a pH of 5.51. As demonstrated here, low concentration of pigment, about 0.5 wt %, can form an adequately stable dispersion in the latex binder solution without separate dispersant. However, higher concentrations of pigment (2-4 wt %) would not disperse adequately, and dispersant was required.

Coating Composition 1 was prepared by stirring together three fluid oz. of Dispersion 1, 10 fluid oz of Prescribe® insecticide (trademark of Gustafson), 2 additional oz of water and isopropyl alcohol (0.5% wt % based on total weight of the coating composition.

Coating Composition 1 was applied to corn seed at a rate of 3 fluid oz of the coating composition per 100 pounds of seed, whereafter the seed was allowed to dry at ambient temperature. As judged by visual inspection and routine handling, the dried seeds were uniformly coated and the coating felt durable and non-sticky.

Example 2

Dispersion 2 was prepared from 100 parts of Latex Binder 1, one part ethylene glycol monobutyl ether and 0.5 parts of Pigment Violet 23 in the same manner as described for Dispersion 1. This demonstrates a violet colored composition, again with a low concentration of pigment and no dispersant. As with dispersion 1, higher concentrations of pigment required dispersant for adequate dispersion quality.

Example 3

Dispersion 3 was prepared by mixing, in order 198.2 parts of deionized water, 142.2 parts of Graft Copolymer 1 solution, 33.3 parts of Latex Binder 1 and 6.7 parts of Surfynol® 104 DPM (surfactant from Air Products, Allentown, Pa., USA). When these ingredients were thoroughly mixed, 133.4 parts of Pigment Violet 23 was added, slowly, after which the mixture was stirred under high shear with a high speed disperser. Another 20.5 gms deionized water was added and the mixture was transferred to a Eiger mill and milled with 0.6-0.8 mm zirconia grinding media. At the end of the milling cycle another 126.7 parts of deionized water was added, followed by another brief period of milling. After filtration through 5 micron paper, the dispersion had a viscosity (Brookfield viscometer, UL adapter, 25° C.) of 28.3 cps and a pH of 7.5.

Coating Composition 3 (containing 4 wt % PV 23) was prepared by mixing, in order, 199.4 parts of Dispersion 3, 10 parts of butyl cellosolve and 790.6 parts of Latex Binder 1. After straining through a 250 micron paint strainer, the resulting coating composition had a viscosity (Brookfield viscometer, RV#2 Spindle, @100 rpm, 25° C.) of 97 cps, and a pH of 8.56. In the presence of graft copolymer dispersant, stable, high pigment content compositions were achieved.

Example 4

Coating composition 4 was prepared from 43.9 parts of Dispersion 4 from Example 4, 2.2 parts butyl cellosolve, 2.2 parts Surfynol® 104 BC (surfactant from Air Products), and 171.7 parts Latex Binder 1 in a manner a similar Coating Composition 3 in the previous example. This mixture was stirred with Poncho 1250 to make the final composition. Coating composition 5 was applied to hybrid seed corn at a rate of 1.5 fluid oz./100 pounds of seed. The coated seed had very good appearance (even coating, stronger color).

Example 5

Coating Composition 5 was prepared from 43.87 parts of Dispersion 3, 2.2 parts butyl cellosolve, 2.2 parts Surfynol 104 BC, and 171.7 parts Latex Binder 1 in a manner a similar Coating Composition 3 in the Example 3. This mixture was stirred with was mixed with Poncho 1250 to make the final composition. Coating composition 5 was applied to hybrid seed corn at use rates of 1.5 fluid oz./100 pounds of seed. The coated seed had very good appearance (even coating, stronger color).

Example 6

Dispersion 6 was prepared by mixing, under low shear, 255.8 parts of deionized water, 111.2 parts of Graft Copolymer 1, 33.3 parts of Latex Binder and 6.7 parts of Surfynol® 104 DPM (surfactant from Air Products). To the mixture was added, slowly, 133.4 parts of Pigment Red 48:2. After the pigment addition was complete, the mixture was stirred under high shear with a high speed disperser. Another 101.6 parts of deionized water was added and the mixture was transferred a sand mill and milled with 0.6-0.8 mm zirconia grinding media. At the end of the grind cycle another 25.1 parts of deionized water was added, followed another 15 minutes of grinding and discharge of the batch. After filtration through 5 micron filter paper, the resulting dispersion had a viscosity (Brookfield viscometer, 00 Spindle at 100 rpm, 25° C.) of 192 cps and a pH or 7.81

Application of Treated Seed

Coated seeds as disclosed in the examples herein before were planted in test plots and an assessed for germination. The germination of the coated seeds was a good as or better than control samples. Also, the coated seeds handled well in the application equipment in that they resisted dust formation and flowed well without sticking.

The invention claimed is:

1. A seed coating composition comprising an aqueous carrier, a pigment colorant, a graft copolymer dispersant, and at least one of a fungicide, an insecticide, a rodenticide, nematocide or bird repellent, wherein:
   the dispersant is a graft copolymer having a weight average molecular weight of about 5,000-100,000 and comprising a polymeric backbone and macromonomer side chains attached to the backbone, wherein:
   (1) the polymeric backbone is hydrophobic in comparison to the side chains and contains polymerized ethylenically unsaturated hydrophobic monomers and present up to 20% by weight, based on the weight of the graft copolymer, of polymerized ethylenically unsaturated acid containing monomers; and
   (2) the sidechains are hydrophilic macromonomers that are attached to the backbone at a single terminal point and contain polymerized ethylenically unsaturated monomers and 2-100% by weight, based on the weight of the macromonomer, of polymerized ethylenically unsaturated acid containing monomers and have a weight average molecular weight of about 1,000-30,000; and
   wherein the acid groups of the graft copolymer are neutralized with an inorganic base or an amine.

2. A method of coating seeds comprising mixing seed with a coating composition according to claim 1 and optionally drying the seed to remove the aqueous carrier.

3. A coated seed formed by a method comprising mixing seed with a seed coating composition comprising an aqueous carrier, a pigment colorant and a graft copolymer dispersant, wherein the dispersant is a graft copolymer having a weight average molecular weight of about 5,000-100,000 and comprising a polymeric backbone and macromonomer side chains attached to the backbone, wherein:
   (1) the polymeric backbone is hydrophobic in comparison to the side chains and contains polymerized ethylenically unsaturated hydrophobic monomers and present up to 20% by weight, based on the weight of the graft copolymer, of polymerized ethylenically unsaturated acid containing monomers; and
   (2) the sidechains are hydrophilic macromonomers that are attached to the backbone at a single terminal point and contain polymerized ethylenically unsaturated monomers and 2-100% by weight, based on the weight of the macromonomer, of polymerized ethylenically unsaturated acid containing monomers and have a weight average molecular weight of about 1,000-30,000; and
   wherein the acid groups of the graft copolymer are neutralized with an inorganic base or an amine.

4. The coated seed of claim 3 further comprising at least one of a fungicide, an insecticide, a rodenticide, nematocide, miticide or bird repellent.

* * * * *